US011628032B2

(12) United States Patent
Hayden et al.

(10) Patent No.: US 11,628,032 B2
(45) Date of Patent: Apr. 18, 2023

(54) STRESS-ABSORBING BUFFER ZONE FOR SEALED TRAY

(71) Applicant: MEDTRONIC VASCULAR, INC., Santa Rosa, CA (US)

(72) Inventors: Thomas Hayden, Turloughmore (IE); Joshua Hillas, Galway (IE); Martin Bernard Patten, Mayo (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 349 days.

(21) Appl. No.: 16/941,652

(22) Filed: Jul. 29, 2020

(65) Prior Publication Data
US 2021/0030506 A1    Feb. 4, 2021

Related U.S. Application Data

(60) Provisional application No. 62/881,401, filed on Aug. 1, 2019.

(51) Int. Cl.
*B65D 77/20* (2006.01)
*A61B 50/33* (2016.01)
(Continued)

(52) U.S. Cl.
CPC .............. *A61B 50/33* (2016.02); *A61L 2/206* (2013.01); *A61L 2/26* (2013.01); *B65D 77/2024* (2013.01);
(Continued)

(58) Field of Classification Search
CPC .... B65D 77/20; B65D 77/2024; A61B 50/33; A61B 2050/0066; A61L 2/206;
(Continued)

(56) References Cited

U.S. PATENT DOCUMENTS

| 4,466,552 A | 8/1984 | Butterworth et al. |
| 5,118,002 A * | 6/1992 | Sugiyama ............. B29C 66/723 220/276 |

(Continued)

FOREIGN PATENT DOCUMENTS

| DE | 10 2015 205221 A1 | 9/2016 |
| EP | 0344340 A1 | 12/1989 |
| JP | 55-33298 U | 3/1980 |

OTHER PUBLICATIONS

International Search Report dated Oct. 22, 2020 in corresponding International Patent Application No. PCT/US2020/044494.
(Continued)

*Primary Examiner* — Luan K Bui
(74) *Attorney, Agent, or Firm* — Medler Ferro Woodhouse & Mills PLLC (57) ABSTRACT

A package includes a tray and a cover configured to seal an open end of the tray when the cover is assembled onto the tray. The tray has a flange extending about a periphery at the open end of the tray. A continuous barrier seal is formed between the flange and the cover when the cover is assembled onto the tray, and a discontinuous sacrificial seal is also formed between the flange and the cover when the cover is assembled onto the tray. The discontinuous sacrificial seal is configured to absorb stress applied to the flange. The continuous barrier seal is disposed closer to an inner periphery of the flange than the discontinuous sacrificial seal. Holes are formed on the corners of the flange, and the holes are spaced apart from the discontinuous sacrificial seal.

20 Claims, 4 Drawing Sheets

(51) Int. Cl.
*A61L 2/20* (2006.01)
*A61L 2/26* (2006.01)
*A61B 50/00* (2016.01)
*A61L 101/44* (2006.01)

(52) U.S. Cl.
CPC ... *A61B 2050/0066* (2016.02); *A61L 2101/44* (2020.08); *A61L 2202/182* (2013.01); *A61L 2202/24* (2013.01)

(58) Field of Classification Search
CPC .. A61L 2/26; A61L 2101/44; A61L 2202/182; A61L 2202/24
USPC ........... 220/359.1, 359.4; 206/363, 368, 370, 206/438
See application file for complete search history.

(56) References Cited

U.S. PATENT DOCUMENTS

| | | | | |
|---|---|---|---|---|
| 5,334,405 A | * | 8/1994 | Gorlich | B65D 81/2076 53/433 |
| 5,348,752 A | * | 9/1994 | Gorlich | B65B 7/168 229/123.1 |
| 5,916,614 A | * | 6/1999 | Gorlich | B65B 7/168 229/123.1 |
| 6,056,138 A | | 5/2000 | Chen | |
| 9,023,411 B2 | | 5/2015 | Määttä et al. | |
| 2003/0056475 A1 | * | 3/2003 | Nakabayashi | B29C 66/7234 53/485 |
| 2005/0103666 A1 | * | 5/2005 | Grimard | A61L 2/183 206/438 |
| 2009/0250466 A1 | * | 10/2009 | Fujimura | B29C 66/81465 220/359.1 |
| 2011/0086141 A1 | | 4/2011 | Strilich et al. | |
| 2011/0127188 A1 | * | 6/2011 | Thompson | B65D 77/20 206/524.6 |
| 2016/0023820 A1 | | 1/2016 | Minnette et al. | |
| 2017/0283129 A1 | | 10/2017 | Charron | |

OTHER PUBLICATIONS

Written Opinion of the International Searching Authority dated Oct. 22, 2020 in corresponding International Patent Application No. PCT/US2020/044494.

* cited by examiner

STRESS-ABSORBING BUFFER ZONE FOR SEALED TRAY

CROSS-REFERENCE TO RELATED APPLICATIONS

This application claims the benefit of U.S. Provisional Patent Application Ser. No. 62/881,401, filed Aug. 1, 2019, which is hereby incorporated by reference in its entirety for all purposes.

FIELD OF THE INVENTION

The present disclosure relates to packaging for medical supplies.

BACKGROUND OF THE INVENTION

Packages may be used to house medical supplies in a sterile environment. In addition to helping to protect the medical supplies from damage that may be caused by handling or storage, packages may help preserve the sterility of medical supplies up to the time of use. For example, a package may house a medical device or another medical supply within a sealed space, and the medical package, including the medical device or other medical supply, may be sterilized prior to distribution. Thus, the package may maintain the sterility of medical supplies within a sealed environment prior to use of the medical device or other medical supply. At the time of use, a clinician may retrieve the medical device or other medical supply from the package by opening the package in a sterile environment to help preserve the sterility of the medical supplies.

After a medical device and/or medical supply is sterilized within a sealed package, the sealed package is shipped or transported to a user and there is a risk that the sealed package may be damaged during transport thereof. More particularly, there is a risk that energy transferred to the sealed package during transportation may be transferred directly to the seal of the sealed package. If the seal of the sealed package is twisted or bent, the seal may be broken or breached, and the contents of the sealed package would no longer be contained in a sterile environment.

Embodiments hereof relate to a sealed package that includes improvements for protecting the seal of the sealed package during transport thereof.

SUMMARY OF THE INVENTION

Embodiments hereof relate to a package configured for the sterility of medical supplies. The package includes a tray and a cover. The tray has at least one side wall defining an open end of the tray, a base panel opposite the open end, and a flange extending about a periphery of the at least one side wall at the open end of the tray. The cover is configured to seal the open end of the tray when the cover is assembled onto the tray. A continuous barrier seal is formed between the flange and the cover when the cover is assembled onto the tray, and a discontinuous sacrificial seal is also formed between the flange and the cover when the cover is assembled onto the tray. The discontinuous sacrificial seal is configured to absorb stress applied to the flange. The continuous barrier seal is disposed closer to an inner periphery of the flange than the discontinuous sacrificial seal.

Embodiments hereof also relate to a package including a tray and a cover removably assembled onto the tray. The cover is configured to seal an open end of the tray when the cover is assembled onto the tray. The tray has at least one side wall defining the open end of the tray, a base panel opposite the open end, and a flange extending about a periphery of the at least one side wall at the open end of the tray. The flange includes a planar top surface and the cover includes a peripheral underside surface configured to mate with the planar top surface of the flange of the tray. A continuous barrier seal is formed between the planar top surface of the flange and the peripheral underside surface of the cover when the cover is assembled onto the tray. A discontinuous sacrificial seal is formed between the planar top surface of the flange and the peripheral underside surface of the cover when the cover is assembled onto the tray. The discontinuous sacrificial seal is configured to absorb stress applied to the flange. The continuous barrier seal is disposed closer to the at least one side wall of the tray than the discontinuous sacrificial seal.

Embodiments hereof also relate to a package including a tray and a cover. The tray has at least one side wall defining an open end of the tray, a base panel opposite the open end, and a flange extending about a periphery of the at least one side wall at the open end of the tray. The cover is configured to seal the open end of the tray when the cover is assembled onto the tray. The flange includes a planar top surface and the cover includes a peripheral underside surface configured to mate with the planar top surface of the flange of the tray. A continuous barrier seal is formed between the planar top surface of the flange and the peripheral underside surface of the cover when the cover is assembled onto the tray. The continuous barrier seal is configured to provide a bacterial barrier when the cover is assembled onto the tray. A discontinuous sacrificial seal is also formed between the planar top surface of the flange and the peripheral underside surface of the cover when the cover is assembled onto the tray. The discontinuous sacrificial seal is configured to absorb stress applied to the flange. At least one hole is formed on the planar top surface of the flange. The at least one hole is spaced apart from the discontinuous sacrificial seal. The continuous barrier seal is disposed closer to an inner periphery of the flange than the discontinuous sacrificial seal and is disposed closer to the inner periphery of the flange than the at least one hole.

BRIEF DESCRIPTION OF THE DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Embodiments hereof relate to packages that may be used to house and protect one or more medical supplies before use. Such packages often include a hermetic or barrier seal that maintains sterility and integrity of the medical supplies.

More particularly, embodiments hereof relate to a package 100 having a stress-absorbing buffer or crumple zone 101 on a flange 112 of the package 100 that is configured to distribute the stress caused by transportation so that the stress is not concentrated on a continuous barrier seal 124 of the package 100. The continuous barrier seal 124 is a critical hermetic seal that maintains the sterility and integrity of a medical supply housed within the package 100. The stress-absorbing buffer or crumple zone 101 is the peripheral portion or region outside of the continuous barrier seal 124, and provides protection to the continuous barrier seal 124 of the package 100 and in turn the sterilized medical supplies housed within the package 100. Features of the stress-absorbing buffer or crumple zone 101 will be described in more detail herein.

Figure 1:
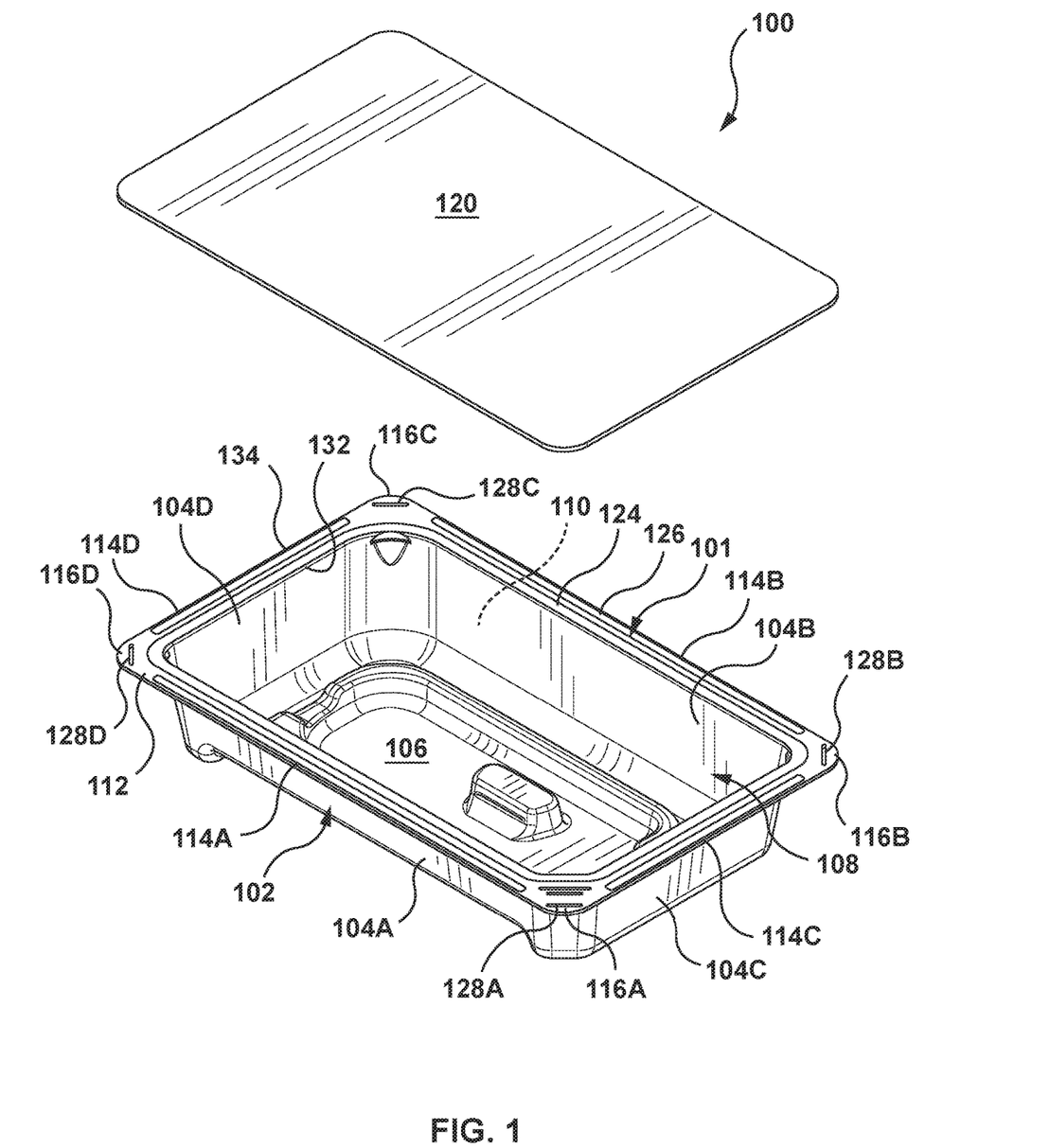
FIG. 1 is an exploded perspective view of a package for medical supplies according to an embodiment hereof, wherein the package includes a tray and a cover configured to seal an open end of the tray when the cover is assembled onto the tray.
Figure 2:
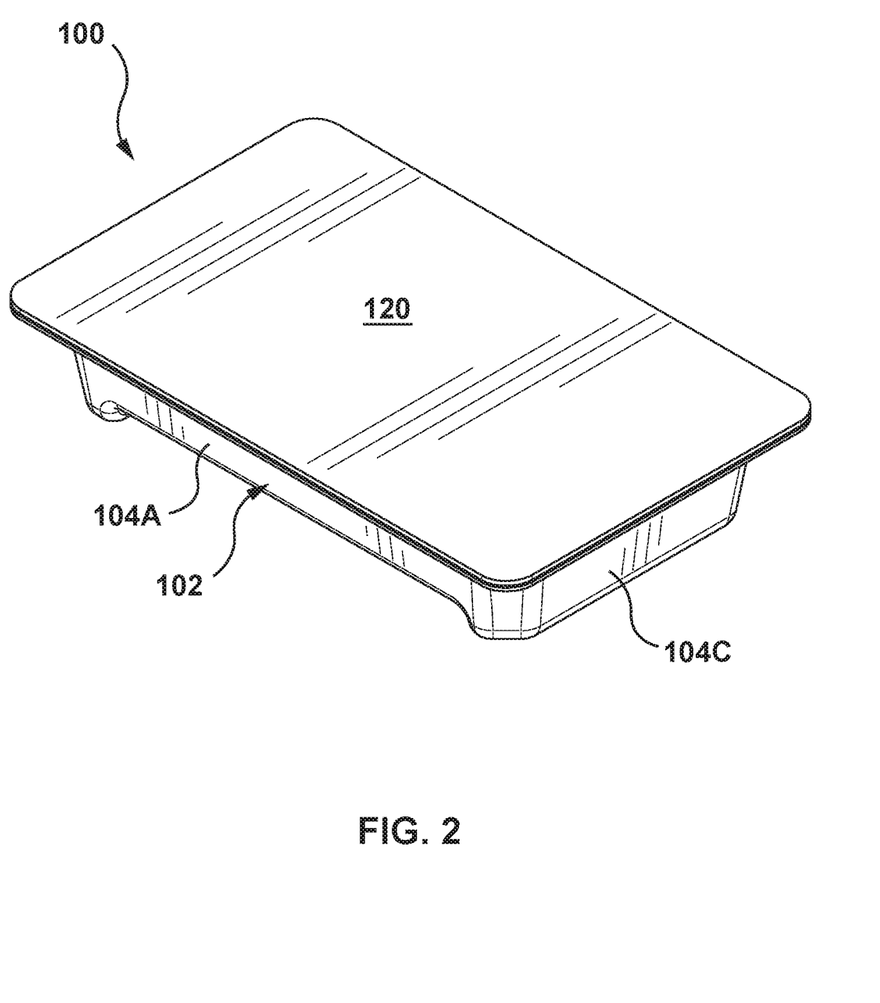
FIG. 2 is a perspective view of the package of FIG. 1, wherein the cover is assembled onto the tray.
Figure 3:
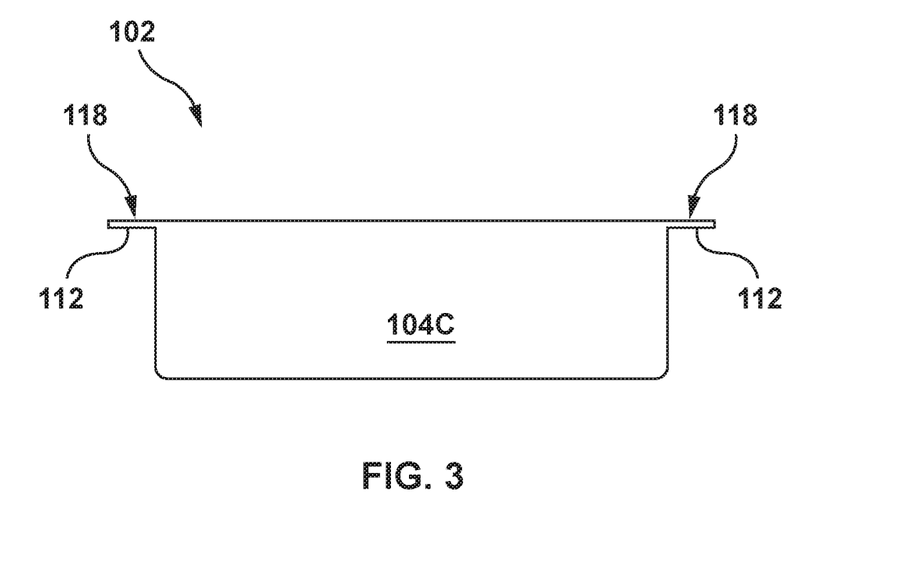
FIG. 3 is a side view of the tray of the package of FIG. 1.
Figure 4:
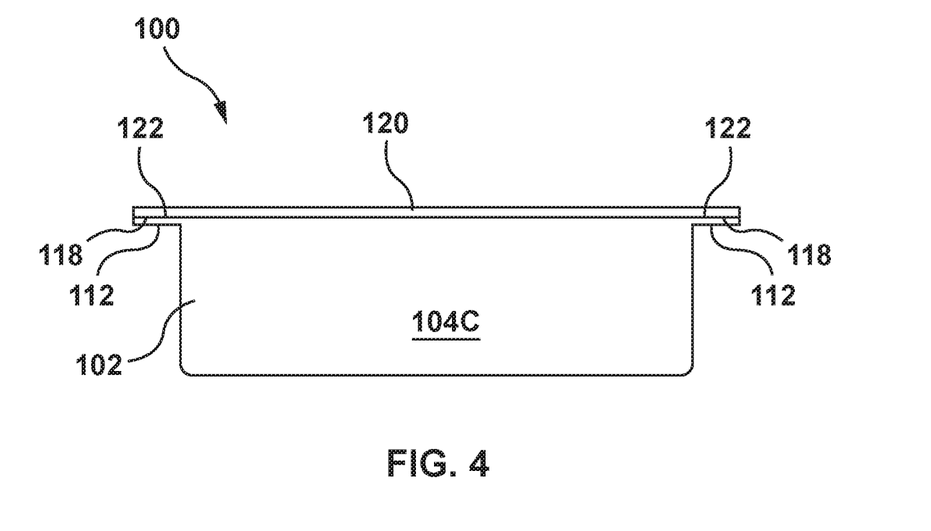
FIG. 4 is a side view of the package of FIG. 1, wherein the cover is assembled onto the tray.
Figure 5:
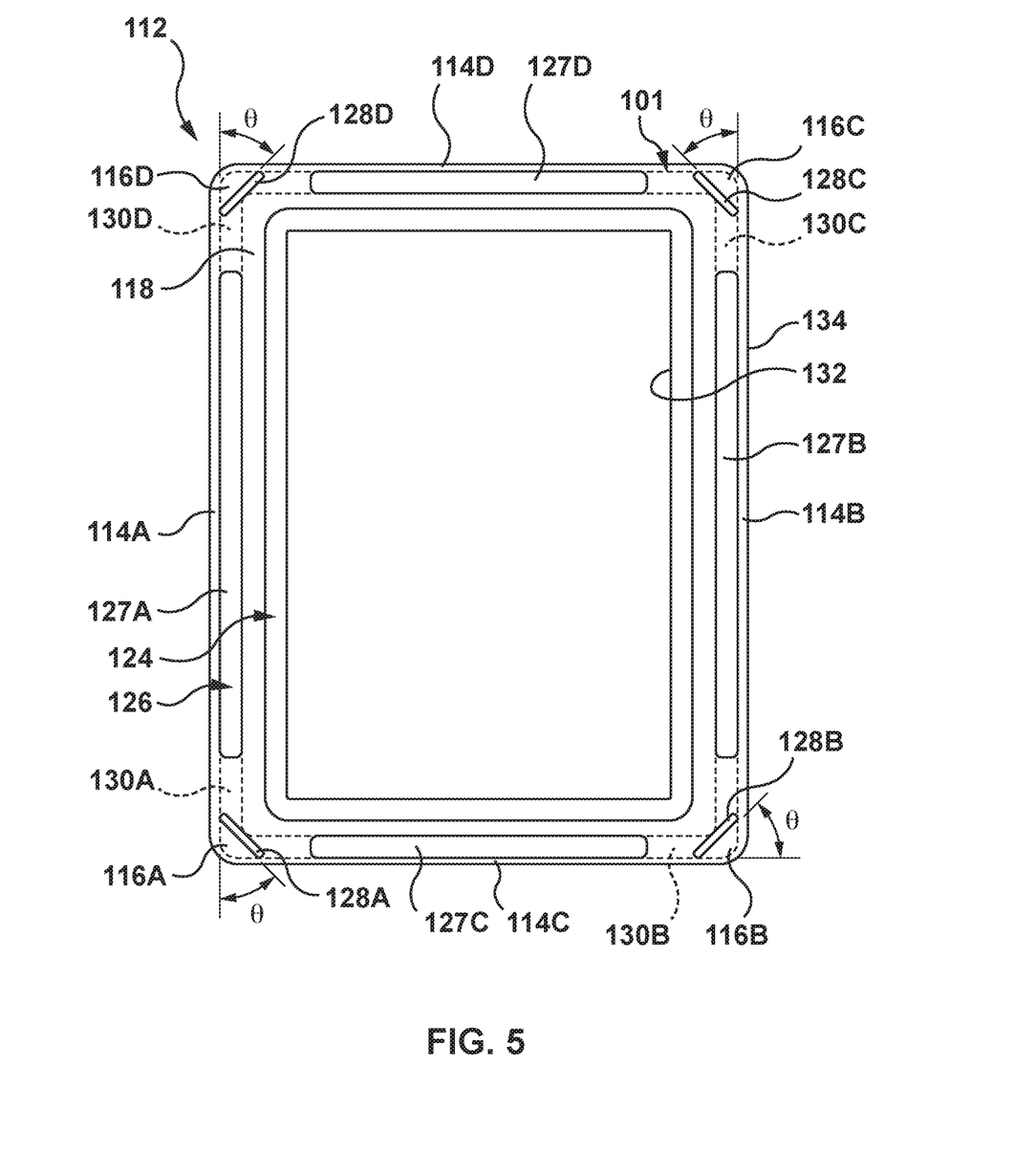
FIG. 5 is a top view of a flange of the tray of the package of FIG. 1.

Turning now to the figures, FIG. 1 is an exploded perspective view of the package 100 showing a tray 102 and a cover 120 that is configured to seal an open end 108 of the tray 102 when the cover 120 is assembled onto the tray 102. FIGS. 2 and 4 are perspective and side views, respectively, of the package 100 with the cover 120 assembled onto the tray 102. FIG. 3 is a side view of the tray 102 without the cover 120 assembled thereon, while FIG. 5 is a top view of the flange 112 of the tray 102. The tray 102 has at least one sidewall defining the open end 108 of the tray 102, and a base panel 106 that is opposite the open end 108. The cover 120 is spaced apart from but extends generally parallel to the base panel 106. In an embodiment, the package 100 and the tray 102 each have a rectangular configuration and the tray 102 includes a total of four sidewalls. More particularly, the tray 102 includes a first sidewall 104A, a second sidewall 104B opposing the first sidewall 104A, a third sidewall 104C, and a fourth sidewall 104D opposing the third sidewall 104C (collectively referred to as "the sidewalls"). The sidewalls 104A, 104B, 104C, 104D are integrally formed with the base panel 106 and extend generally perpendicular from the base panel 106 towards the cover 120. "Generally perpendicular" as used herein includes sidewalls that extend perpendicular from the base panel 106 or extend in an upward direction or vertically at an angle from the base panel 106. For example, the sidewalls 104A, 104B, 104C, 104D may extend upwards or vertically at an angle between 60 and 120 degrees from the base panel 106. Further, a different number of sidewalls may be required to enclose the package 100 depending on the shape of the base panel 106 and the cover 120. For example, when the cover 120 and the base panel 106 are of a circular or oval shape, a single sidewall may be utilized to enclose the package 100.

The sidewalls 104A, 104B, 104C, 104D and the base panel 106 collectively form or define an interior cavity or space 110 which receives the medical device or other medical supply to be sterilized. The interior cavity 110 of the tray 102 may be formed into any suitable shape and size. The shape and size of the interior cavity 110 depends upon the shape and size of the medical device or other medical supply that is being housed within the tray 102. In the embodiment shown in FIG. 1, the tray 102 is generally rectangular in shape and has a generally rectangular shaped interior cavity 110. However, the interior cavity 110 may take on any shape or size sufficient for its intended application. In an embodiment, the interior cavity 110 of the tray 102 may be a custom geometry to accommodate a particular type of medical device or other medical supply.

The tray 102 includes the flange 112 that extends outwardly from of the sidewalls 104A, 104B, 104C, 104D and extends around or about a periphery of the sidewalls 104A, 104B, 104C, 104D at the open end 106 of the tray 102. The flange 112 of the tray 102 thus surrounds the open end 106 of the tray 102. The flange 112 is integrally formed with the sidewalls 104A, 104B, 104C, 104D and extends outwardly from the sidewalls 104A, 104B, 104C, 104D in a direction away from the base panel 106. The flange 112 includes a planar top surface 118. In an embodiment, the planar top surface 118 of the flange 112 is spaced apart and parallel to the base panel 106 as best shown in the side views of FIGS. 3 and 4. The planar top surface 118 of the flange 112 however may alternatively be spaced apart but extend at an angle relative to the base panel 106. The flange 112 includes an inner periphery 132 and an outer periphery 134, and the planar top surface 118 extends between the inner and outer peripheries 132, 134. In an embodiment, the flange 112 has a rectangular configuration including four edges and four corners integrally formed between the edges. More particularly, the flange 112 includes a first edge 114A, a second edge 114B opposing the first edge 114A, a third edge 114C, a fourth edge 114D opposing the third edge 114C. A first corner 116A extends between the first and third edges 114A, 114C, respectively. A second corner 116B extends between the third and second edges 114C, 114B, respectively. A third corner 116C extends between the second and fourth edges 114B, 114D. A fourth corner 116D extends between the fourth and first edges 114D, 114A.

The tray 102 is formed as a one-piece component such that the base panel 106, the sidewalls 104A, 104B, 104C, 104D, and the flange 112 are integrally formed in a one-piece construction. The tray 102 may be formed from an injection molded plastic material such as but not limited to polypropylene, polycarbonate (PC), acrylonitrile butadiene styrene (ABS), a PC/ABS blend, nylon, polyvinyl chloride (PVC), and a polyethylene terephthalate glycol (PETG) material. In an embodiment, the tray 102 can be formed from a transparent or clear plastic material such that the medical device or supply housed therein is visible. Further, in an embodiment, the material of the tray 102 is substantially impervious or impermeable to one or more of gas, moisture, vapor, fluids, particulates, microorganism, or contaminants.

The cover 120 is of a size and shape that is configured to seal the open end 108 of the tray 102 when the cover 120 is assembled onto the tray 102, as best shown on the perspective view of FIG. 2. In an embodiment, the cover 120 and the base panel 106 of the tray 102 is of the same shape (e.g., rectangular in the embodiment of FIGS. 1-5), although the cover 120 may have a different shape so long as it is configured to seal the open end 108 of the tray 102 when the cover 120 is assembled onto the tray 102. In an embodiment, the cover 120 is generally the same size and shape (e.g., rectangular in the embodiment of FIGS. 1-5) as the outer periphery 134 of the flange 112. As best shown in the side view of FIG. 4, the cover 120 includes a peripheral underside surface 122 that is configured to mate with the planar top surface 118 of the flange 112 of the tray 102. The cover 120 encloses the medical device or other medical supply within the interior space 110 of the tray 102.

In an embodiment, the cover 120 is formed from a sheet material having a breathable membrane that is impermeable to microorganisms but is permeable to gases. The breathable membrane comprises a breathable material through which a gas, such as a sterilizing gas, can be introduced into the interior of the package 100.

More particularly, generally, it is desirable to sterilize medical instruments and devices after packaging and prior to being sent to the end user. Forms of sterilization include irradiation, autoclaving, and treatment with a sterilizing gas, such as ethylene oxide. Typically, treatment with a sterilizing gas is used to sterilize medical supplies. The package 100 may be sterilized after the medical supply or supplies are positioned within the interior space 110 of the package 100. In an embodiment, the package 100 may be sterilized by exposing the package 100 (having the cover 120 sealingly attached to the tray 102 as will be described in more detail herein) to a sterilizing agent. For example, the sterilizing agent may include a gaseous or vapor composition include one or more of a gas, an aerosolized component, a suspended component, droplets, or the like. In some examples, the sterilizing agent includes ethylene oxide gas. The sterilizing gas can be introduced into the interior space 110 of the package 102 through the breathable membrane of the cover 120 for sterilizing the contents (i.e., the medical supplies) of the package.

Suitable materials for the cover 120 include any material that is a barrier to microorganisms, but is permeable to gases including oxygen, carbon dioxide, and various sterilization gases. For example, suitable materials for the cover 120 may include a nonwoven sheet material such as TYVEK (spunbond polyethylene), medical grade paper, microbial barrier membranes, and other porous materials that limit the passage of microbes. TYVEK is permeable to sterilizing gases such as vapor phase hydrogen peroxide, ozone, ethylene oxide, and steam, and yet is impermeable to potentially contaminating microorganisms. Similarly, medical grade paper is permeable to sterilizing gases such as ethylene oxide, ozone and steam, yet is impermeable to potentially contaminating microorganisms.

In another embodiment, the material for the cover 120 is not required to include a breathable membrane that is a barrier to microorganisms but is permeable to gases. In some applications, sterilization of the contents of the package does not require that a sterilizing gas be introduced into the interior space 110 of the package 102 through the cover 120. Stated another way, a gas path may not be required for sterilization. For example, ionizing radiation including gamma radiation or electron beam may be utilized as a form of sterilization. Both porous and non-porous materials are compatible with such radiation sterilization methods. As such, the cover 120 may be formed from a non-porous plastic material. In an embodiment, the cover 120 can be formed from a transparent or clear plastic material such that the medical device or supply housed therein is visible.

When assembled onto the tray 102 as shown on FIGS. 2 and 4, the cover 120 extends over the open end 108 and the peripheral underside surface 122 is sealingly attached to the planar top surface 118 of the flange 112 of the tray 102. More particularly, the continuous barrier seal 124 is formed between the flange 112 and the cover 120 when the cover 120 is assembled onto the tray 102. Continuous as used herein means that the barrier seal 124 extends around the inner periphery 132 of the flange 112 without gaps or breaks therein and therefore extends around or about the entire open end 106 of the tray 102. The continuous barrier seal 124 attaches the cover 120 and the tray 102 together. For example, in an embodiment, the cover 120 may be heat sealed to the tray 102 to form the continuous barrier seal 124. In another embodiment, an adhesive may be used to form the continuous barrier seal 124. The continuous barrier seal 124 is a hermetic seal such that the environment within the interior space 110 of the package 100 remains relatively constant. Stated another way, the continuous barrier seal 124 ensures that the integrity of the sterile environment within the interior space 110 is not compromised.

As stated above, the package 100 includes the stress-absorbing buffer or crumple zone 101 or region on the flange 112 that is configured to distribute the stress caused by transportation so that the stress is not concentrated on the continuous barrier seal 124 of the package 100. The stress-absorbing buffer or crumple zone 101 includes the peripheral portion or region of the flange 112 outside of the continuous barrier seal 124. More particularly, the stress-absorbing buffer or crumple zone 101 includes a widened planar surface area that includes a secondary or sacrificial seal 126 disposed around the outer periphery 134 of the flange 112 to absorb stress that would otherwise be transferred to the continuous barrier seal 124. The secondary or sacrificial seal 126 functions to cushion the continuous barrier seal 124 and reduce twisting and bending motion of the flange 112. The secondary or sacrificial seal 126 is best shown on FIG. 5.

More particularly, the sacrificial seal 126 is a discontinuous seal formed between the flange 112 and the cover 120 when the cover 120 is assembled onto the tray 102. Non-continuous as used herein means that the sacrificial seal 126 does not extend around the entire outer periphery 134 of the flange 112 but rather includes gaps or breaks therein. The discontinuous sacrificial seal 126 is disposed on each of the first edge 114A, the second edge 114B, the third edge 114C, and the fourth edge 114D of the flange 112, but it is not disposed on each of the first corner 116A, the second corner 116B, the third corner 116C, and the fourth corner 116D of the flange 112. More particularly, in this embodiment in which flange 112 has a rectangular configuration, the discontinuous sacrificial seal 126 includes four generally straight segments 127A, 127B, 127C, 127D. Straight segment 127A is disposed on the first edge 114A of the flange 112, straight segment 127B is disposed on the second edge 114B of the flange 112, straight segment 127C is disposed on the third edge 114C of the flange 112, and straight segment 127D is disposed on the fourth edge 114D of the flange 112.

The straight segments 127A, 127B, 127C, 127D of the discontinuous sacrificial seal 126 are disposed relative to each other to resemble a rectangle, with the corners of such a rectangle not including the discontinuous sacrificial seal 126. The corners of such a rectangle that do not include the discontinuous sacrificial seal 126 are herein referred to as non-seal portions 130A, 130B, 130C, 130D that are disposed between the straight segments 127A, 127B, 127C, 127D of the discontinuous sacrificial seal 126. These non-seal portions 130A, 130B, 130C, 130D are essentially the gaps, spaces, or breaks that make the sacrificial seal 126 discontinuous. The non-seal portions 130A, 130B, 130C, 130D generally are disposed at the corners 116A, 116B, 116C, 116D of the flange 112. More particularly, the non-seal portion 130A extends between straight segments 127A, 127C of the discontinuous sacrificial seal 126 and is disposed on the corner 116A of the flange 112. The non-seal portion 130B extends between straight segments 127C, 127B of the discontinuous sacrificial seal 126 and is disposed on the corner 116B of the flange 112. The non-seal portion 130C extends between straight segments 127B, 127D of the discontinuous sacrificial seal 126 and is disposed on the corner 116C of the flange 112. The non-seal portion 130D extends between straight segments 127D, 127A of the discontinuous sacrificial seal 126 and is disposed on the corner 116D of the flange 112.

Each of the discontinuous sacrificial seal 126 and the continuous barrier seal 124 is disposed on the planar top surface 118 of the flange 112. The discontinuous sacrificial seal 126 is disposed on or along the outer periphery 134 of the flange 112 and the continuous barrier seal 124 is disposed on or along the inner periphery 132 of the flange 112. Stated another way, the continuous barrier seal 124 is disposed closer to the side walls 104A, 104B, 104C, 104D of the tray 102 (and the inner periphery 132 of the flange 112) than the discontinuous sacrificial seal 126. Accordingly, since the discontinuous sacrificial seal 126 is disclosed outside of the continuous barrier seal 124, the discontinuous sacrificial seal 126 is configured to absorb stress that is applied to the flange 112 that would otherwise be transferred to the continuous barrier seal 124. The discontinuous sacrificial seal 126 also functions to stiffen the area outside the continuous barrier seal 124. When stress is applied to the flange 112, deformation of the flange 112 occurs at the stress-absorbing buffer or crumple zone 101 which is the peripheral portion or region of the flange 112 outside of the continuous barrier seal 124. The discontinuous sacrificial seal 126 is configured to preferentially break or peel such that the continuous barrier seal 124 is thereby protected and remains intact. Lastly, the non-seal portions 130A, 130B, 130C, 130D that are disposed between the straight segments 127A, 127B, 127C, 127D of the discontinuous sacrificial seal 126 provide access points for the user to remove or peel away the cover 120 from the tray 102 when it is desired to open the package 100.

In addition to the discontinuous sacrificial seal 126, the stress-absorbing buffer or crumple zone 101 also includes a plurality of holes 128A, 128B, 128C, 128D (collectively referred to herein as holes 128) disposed at strategic locations on the flange 112 to permit controlled deflection or deformation of the package 100. In an embodiment, the holes 128 are cutouts that extend through the entire thickness of the flange 112. In an embodiment hereof, each hole 128 has an oblong or rectangular configuration and is formed on the flange. However, in another embodiment hereof, each hole 128 may have a different configuration such as circular, zigzag, triangular, trapezoidal, or any other configuration suitable to permit controlled deflection or deformation of the package 100. In an embodiment, a hole 128 is positioned on each of the first corner 116A, the second corner 116B, the third corner 116C, and the fourth corner 116D of the flange 112. The holes 128 are spaced apart from the straight segments 127A, 127B, 127C, 127D of the discontinuous sacrificial seal 126. More particularly, the holes 128 are formed on the non-seal portions 130A, 130B, 130C, 130D that are disposed between the straight segments 127A, 127B, 127C, 127D of the discontinuous sacrificial seal 126.

Each hole 128 is angled between the corresponding edges of the flange 112. More particularly, the hole 128A is angled between the first edge 114A and the third edge 114C of the flange 112. The hole 128B is angled between the third edge 114C and the second edge 114B of the flange 112. The hole 128C is angled between the second edge 114B and the fourth edge 114D of the flange 112. The hole 128D is angled between the fourth edge 114D and the first edge 114A of the flange 112. Each pair of adjacent edges of the flange 112 form approximately a ninety degrees angle, and each hole extends at approximately a forty-five degree angle θ as shown on FIG. 5. Approximately as used herein includes a tolerance of five degrees.

The holes 128 are configured to control deflection and/or deformation of the flange 112 outside the continuous barrier seal 124. More particularly, the continuous barrier seal 124 is disposed closer to the side walls 104A, 104B, 104C, 104D of the tray 102 than the holes 128. The holes 128 bias or control deformation of the flange 112 outside the continuous barrier seal 124 because the flange 112 is configured to deform or deflect at the holes 128 rather than along the continuous barrier seal 124. Although the discontinuous sacrificial seal 126 stiffens the flange 112 outside the continuous barrier seal 124, the flange 112 is more flexible at the corners 116A, 116B, 116C, 116D thereof that do not include the discontinuous sacrificial seal 126 and thus these corners may flex and deform without interfering with the integrity of the continuous barrier seal 124 when stress is applied to the flange 112.

In another embodiment (not shown), the holes 128 are depressions or indentations that do not extend through the entire thickness of the flange 112 but rather extend only partially through the thickness of the flange. Such depressions or indentations may also be configured to control deflection and/or deformation of the flange 112 outside the continuous barrier seal 124.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A package configured for the sterility of medical supplies, the package comprising:
   a tray having at least one side wall defining an open end of the tray, a base panel opposite the open end, and a flange extending about a periphery of the at least one side wall at the open end of the tray, the flange including a plurality of edges and a plurality of corners, with each corner of the plurality of corners being formed between adjacent edges of the plurality of edges;
   a cover configured to seal the open end of the tray when the cover is assembled onto the tray;
   a continuous barrier seal formed between the flange and the cover when the cover is assembled onto the tray; and
   a discontinuous sacrificial seal formed between the flange and the cover when the cover is assembled onto the tray, the discontinuous sacrificial seal configured to absorb stress applied to the flange and preferentially break to protect the continuous barrier seal, wherein the continuous barrier seal is disposed closer to an inner periphery of the flange than the discontinuous sacrificial seal, and
   wherein the discontinuous sacrificial seal is disposed on each edge of the plurality of edges, and
   wherein the discontinuous sacrificial seal is not disposed on each corner of the plurality of corners.

2. The package of claim 1, wherein the package has a rectangular configuration and the at least one side wall includes a first sidewall, a second sidewall opposing the first sidewall, a third sidewall, and a fourth sidewall opposing the third sidewall.

3. The package of claim 2, wherein the flange has a rectangular configuration and the plurality of edges includes a first edge, a second edge opposing the first edge, a third edge, and a fourth edge opposing the third edge, and the plurality of corners includes a first corner extending between the first and third edges, a second corner extending between the third and second edges, a third corner extending between the second and fourth edges, and a fourth corner extending between the fourth and first edges.

4. The package of claim 1, wherein a hole is formed on at least one corner of the plurality of corners, the continuous barrier seal being disposed closer to the inner periphery of the flange than the hole.

5. The package of claim 1, wherein a hole is formed on each corner of the plurality of corners, thereby forming a plurality of holes, the continuous barrier seal being disposed closer to the inner periphery of the flange than the plurality of holes.

6. The package of claim 5, wherein the holes are rectangular.

7. The package of claim 1, wherein the cover is formed from a breathable membrane that is impermeable to microorganisms but is permeable to gases.

8. The package of claim 1, wherein each corner of the plurality of corners is configured to provide an access point for a user to peel away the cover from the tray.

9. The package of claim 1, wherein each corner of the plurality of corners is configured to deform without interfering with the continuous barrier seal when stress is applied to the flange.

10. The package of claim 9, wherein each corner of the plurality of corners is more flexible than each edge of the plurality of edges.

11. A package configured for the sterility of medical supplies, the package comprising:
- a tray having a rectangular configuration with a first sidewall, a second sidewall opposing the first sidewall, a third sidewall, and a fourth sidewall opposing the third sidewall defining an open end of the tray, a base panel opposite the open end, and a flange extending about a periphery of the first sidewall, the second sidewall, the third sidewall, and the fourth sidewall at the open end of the tray, wherein the flange includes a planar top surface and has a rectangular configuration, the flange including a first edge, a second edge opposing the first edge, a third edge, a fourth edge opposing the third edge, a first corner extending between the first and third edges, a second corner extending between the third and second edges, a third corner extending between the second and fourth edges, and a fourth corner extending between the fourth and first edges;
- a cover removably assembled onto the tray, the cover configured to seal the open end of the tray when the cover is assembled onto the tray, wherein the cover includes a peripheral underside surface configured to mate with the planar top surface of the flange of the tray;
- a continuous barrier seal formed between the flange and the cover when the cover is assembled onto the tray; and
- a discontinuous sacrificial seal formed between the flange and the cover when the cover is assembled onto the tray, the discontinuous sacrificial seal configured to absorb stress applied to the flange and preferentially break to protect the continuous barrier seal, wherein the continuous barrier seal is disposed closer to the first sidewall, the second sidewall, the third sidewall, and the fourth sidewall of the tray than the discontinuous sacrificial seal, and
- wherein the discontinuous sacrificial seal is disposed on each of the first edge, the second edge, the third edge, and the fourth edge, and
- wherein the discontinuous sacrificial seal is not disposed on each of the first corner, the second corner, the third corner and the fourth corner.

12. The package of claim 11, wherein a hole is formed on at least one of the first corner, the second corner, the third corner, and the fourth corner, the continuous barrier seal being disposed closer to the at least one side wall of the tray than the hole.

13. The package of claim 11, wherein a hole is formed on each of the first corner, the second corner, the third corner, and the fourth corner, thereby forming a plurality of holes, the continuous barrier seal being disposed closer to the inner periphery of the flange than the plurality of holes.

14. The package of claim 13, wherein the holes are rectangular.

15. The package of claim 11, wherein the cover is formed from a breathable membrane that is impermeable to microorganisms but is permeable to gases.

16. A package configured for the sterility of medical supplies, the package comprising:
- a tray having at least one side wall defining an open end of the tray, a base panel opposite the open end, and a flange extending about a periphery of the at least one side wall at the open end of the tray, wherein the flange includes a planar top surface; and
- a cover configured to seal the open end of the tray when the cover is assembled onto the tray, wherein the cover includes a peripheral underside surface configured to mate with the planar top surface of the flange of the tray;
- a continuous barrier seal formed between the planar top surface of the flange and the peripheral underside surface of the cover when the cover is assembled onto the tray, the continuous barrier seal being configured to provide a bacterial barrier when the cover is assembled onto the tray; and
- a discontinuous sacrificial seal formed between the planar top surface of the flange and the peripheral underside surface of the cover when the cover is assembled onto the tray, the discontinuous sacrificial seal configured to absorb stress applied to the flange, wherein the continuous barrier seal is disposed closer to an inner periphery of the flange than the discontinuous sacrificial seal, and
- wherein at least one hole is formed on the planar top surface of the flange, the at least one hole being spaced apart from the discontinuous sacrificial seal and the continuous barrier seal being disposed closer to the inner periphery of the flange than the at least one hole.

17. The package of claim 16, wherein the package has a rectangular configuration and the at least one side wall includes a first sidewall, a second sidewall opposing the first sidewall, a third sidewall, and a fourth sidewall opposing the third sidewall and wherein the flange has a rectangular configuration and includes a first edge, a second edge opposing the first edge, a third edge, a fourth edge opposing the third edge, a first corner extending between the first and third edges, a second corner extending between the third and second edges, a third corner extending between the second and fourth edges, and a fourth corner extending between the fourth and first edges, and wherein the discontinuous sacrificial seal is disposed on each of the first edge, the second edge, the third edge, and the fourth edge.

18. The package of claim 17, wherein the discontinuous sacrificial seal is not disposed on each of the first corner, the second corner, the third corner, and the fourth corner and the at least one hole includes a hole formed on each of the first corner, the second corner, the third corner, and the fourth corner.

19. The package of claim 18, wherein the holes are rectangular.

20. The package of claim 16, wherein the flange including a plurality of edges and a plurality of corners, with each corner of the plurality of corners being formed between adjacent edges of the plurality of edges, and wherein the at least one hole is formed on at least one corner of the plurality of corners.

* * * * *